(12) United States Patent
Brannan

(10) Patent No.: US 8,328,801 B2
(45) Date of Patent: *Dec. 11, 2012

(54) SURFACE ABLATION ANTENNA WITH DIELECTRIC LOADING

(75) Inventor: Joseph D. Brannan, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 652 days.

This patent is subject to a terminal disclaimer.

(21) Appl. No.: 12/542,348

(22) Filed: Aug. 17, 2009

(65) Prior Publication Data

US 2011/0040300 A1    Feb. 17, 2011

(51) Int. Cl.
*A61B 18/18* (2006.01)

(52) U.S. Cl. .................. 606/41; 607/154; 607/156

(58) Field of Classification Search .......... 606/32, 606/33, 34, 41; 607/101, 154, 156
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,776,086 A * | 10/1988 | Kasevich et al. | 29/828 |
| 4,798,215 A | 1/1989 | Turner | |
| 4,823,812 A * | 4/1989 | Eshel et al. | 607/156 |
| 5,097,844 A | 3/1992 | Turner | |
| 5,301,687 A | 4/1994 | Wong et al. | |
| 5,405,346 A | 4/1995 | Grundy et al. | |
| 5,417,210 A | 5/1995 | Funda et al. | |
| 5,599,295 A | 2/1997 | Rosen et al. | |
| 5,720,718 A | 2/1998 | Rosen et al. | |
| 6,031,375 A | 2/2000 | Atalar et al. | |
| 6,123,701 A | 9/2000 | Nezhat | |
| 6,289,249 B1 | 9/2001 | Arndt et al. | |
| 6,325,796 B1 | 12/2001 | Berube et al. | |
| 6,375,606 B1 | 4/2002 | Garibaldi et al. | |
| 6,398,781 B1 | 6/2002 | Goble et al. | |

(Continued)

FOREIGN PATENT DOCUMENTS

DE           390937           3/1924

(Continued)

OTHER PUBLICATIONS

U.S. Appl. No. 10/244,346, filed Sep. 16, 2002, Abandoned.

(Continued)

*Primary Examiner* — Michael Peffley
*Assistant Examiner* — Jocelyn D Ram

(57) ABSTRACT

An electrosurgical device for directing energy to a target volume of tissue includes a coaxial feedline having an inner conductor, an outer conductor coaxially disposed around the inner conductor, and a dielectric material disposed therebetween. An elongated electrically-conductive member is longitudinally disposed at a distal end of the inner conductor; a balun structure is disposed on the outer conductor. An electrically-conductive cylinder is coaxially disposed around a distal portion of the balun structure and a dielectric structure is disposed substantially adjacent to a distal end of the electrically-conductive cylinder and configured to extend to a distal end of the electrically-conductive member. An elongated handle assembly is coaxially disposed around a portion of the outer conductor proximal to the dielectric structure and a shell assembly is disposed at a distal end of the elongated handle assembly. A portion of the shell assembly is configured to extend distally beyond the distal end of the electrically-conductive member.

19 Claims, 10 Drawing Sheets

U.S. PATENT DOCUMENTS

| | | |
|---|---|---|
| 6,451,015 B1 | 9/2002 | Rittman, III et al. |
| 6,503,248 B1 | 1/2003 | Levine |
| 6,582,427 B1 | 6/2003 | Goble et al. |
| 6,603,994 B2 | 8/2003 | Wallace et al. |
| 6,723,091 B2 | 4/2004 | Goble et al. |
| 6,725,080 B2 | 4/2004 | Melkent et al. |
| 7,301,131 B2* | 11/2007 | Gauthier et al. ............... 219/679 |
| 7,311,703 B2* | 12/2007 | Turovskiy et al. ............... 606/33 |
| 7,439,736 B2 | 10/2008 | Meaney et al. |
| 7,467,015 B2 | 12/2008 | Van der Weide |
| 7,565,207 B2 | 7/2009 | Turner et al. |
| 7,642,451 B2 | 1/2010 | Bonn |
| 7,875,024 B2 | 1/2011 | Turovskiy et al. |
| 8,035,570 B2 | 10/2011 | Prakash et al. |
| 8,059,059 B2 | 11/2011 | Bonn |
| 8,118,808 B2 | 2/2012 | Smith et al. |
| 2002/0022836 A1 | 2/2002 | Goble et al. |
| 2003/0083654 A1* | 5/2003 | Chin et al. ........................ 606/41 |
| 2003/0125730 A1 | 7/2003 | Berube et al. |
| 2003/0153908 A1 | 8/2003 | Goble et al. |
| 2004/0097805 A1 | 5/2004 | Verard et al. |
| 2004/0242992 A1 | 12/2004 | Hareyama |
| 2007/0106332 A1* | 5/2007 | Denker et al. ..................... 607/2 |
| 2007/0233057 A1 | 10/2007 | Konishi |
| 2009/0187180 A1 | 7/2009 | Brannan |
| 2011/0034913 A1* | 2/2011 | Brannan ........................ 606/33 |
| 2011/0034917 A1* | 2/2011 | Brannan ........................ 606/41 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0-572 131 | 12/1993 |
| EP | 0 836 868 | 4/1998 |
| EP | 1 034 748 | 9/2000 |
| EP | 1 159 926 | 5/2001 |
| EP | 1186274 | 8/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| GB | 2045620 | 11/1980 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | 93/22977 | 11/1993 |
| WO | WO97/41924 | 11/1997 |
| WO | WO97/43971 | 11/1997 |
| WO | WO00/48672 | 8/2000 |
| WO | 00/53112 | 9/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |
| WO | 2006/084676 | 8/2006 |
| WO | WO 2008/012827 | 1/2008 |
| WO | WO 2009/128940 | 10/2009 |

OTHER PUBLICATIONS

U.S. Appl. No. 12/023,606, filed Jan. 31, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.

U.S. Appl. No. 12/395,034, filed Feb. 27, 2009.
U.S. Appl. No. 12/399,222, filed Mar. 6, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210, abstract only.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184, abstract only.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. 1, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar vessel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
S. Humphries Jr. et al., "Finite•Element Codes to Model Electrical Heating and Non•L1near Thermal Transport in Biological Media", Proc. ASME HTD-355, 131 (1997).
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.

European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts". Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report for European Application No. 10008533 dated Dec. 20, 2010. (9 pages).
Extended European Search Report for European Application No. EP10014705 dated Apr. 27, 2011 (5 pages).
U.S. Appl. No. 08/483,742, filed Jun. 7, 1995.
U.S. Appl. No. 08/136,098, filed Oct. 14, 1993.
Bulletin of the American Physical Society, vol. 47, No. 5, Aug. 2002, p. 41.

* cited by examiner

SURFACE ABLATION ANTENNA WITH DIELECTRIC LOADING

BACKGROUND

1. Technical Field

The present disclosure relates to electrosurgical devices suitable for use in surface ablation applications and, more particularly, to electrosurgical devices with directional radiation patterns.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis.

A microwave transmission line typically includes a thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, e.g., a length of transmission line or coaxial cable, is provided with a plurality of openings through which energy "leaks" or radiates away from the guiding structure. This type of construction is typically referred to as a "leaky coaxial" or "leaky wave" antenna.

Some ablation targeted lesions are too small or too hard to be punctured by an ablation probe. In these cases, doctors may place the probe as close as possible to the lesion and perform an ablation. With non-directional ablation probes, the ablation may radiate to both sides of the probe which may damage healthy tissue located on the non-tumor side of the radiating section.

During certain procedures, it can be difficult to assess the extent to which the microwave energy will radiate into the surrounding tissue, making it difficult to determine the area or volume of surrounding tissue that will be ablated.

SUMMARY

The present disclosure relates to a device for directing energy to a target volume of tissue including a coaxial feedline having an inner conductor, an outer conductor coaxially disposed around the inner conductor, and a dielectric material disposed therebetween. An elongated electrically-conductive member is longitudinally disposed at a distal end of the inner conductor. A balun structure is disposed on the outer conductor. The device includes an electrically-conductive cylinder coaxially disposed around a distal portion of the balun structure, and a dielectric structure disposed substantially adjacent to a distal end of the electrically-conductive cylinder, wherein the dielectric structure longitudinally extends from the distal end of the electrically-conductive cylinder to a distal end of the electrically-conductive member. The device also includes an elongated handle assembly coaxially disposed around a portion of the outer conductor at a distal end of the coaxial feedline, wherein the handle assembly is disposed proximal to the dielectric structure, and a shell assembly disposed at a distal end of the handle assembly, wherein a portion of the shell assembly extends distally beyond the distal end of the electrically-conductive member.

The present disclosure also relates to a method for manufacturing an electrosurgical device including the steps of providing a coaxial feedline having an inner conductor, an outer conductor, and a dielectric material disposed therebetween, and joining an electrically-conductive member to a distal end of the inner conductor at a distal end of the coaxial feedline. The method also includes the steps of: joining a balun structure to a distal portion of the outer conductor; joining an electrically-conductive cylinder to distal portion of the balun structure; forming a dielectric structure disposed substantially adjacent to a distal end of the electrically-conductive cylinder, wherein the dielectric structure longitudinally extends from the distal end of the electrically-conductive cylinder to a distal end of the electrically-conductive member; joining an elongated handle assembly to the outer conductor at a distal end of the coaxial feedline, wherein the handle assembly is disposed proximal to the dielectric structure; and joining a shell assembly to a distal end of the elongated handle assembly, wherein a portion of the shell assembly extends distally beyond the distal end of the electrically-conductive member.

BRIEF DESCRIPTION OF THE DRAWINGS

Objects and features of the presently disclosed surface ablation antenna assemblies will become apparent to those of ordinary skill in the art when descriptions of various embodiments thereof are read with reference to the accompanying drawings, of which.

DETAILED DESCRIPTION

Figure 1:
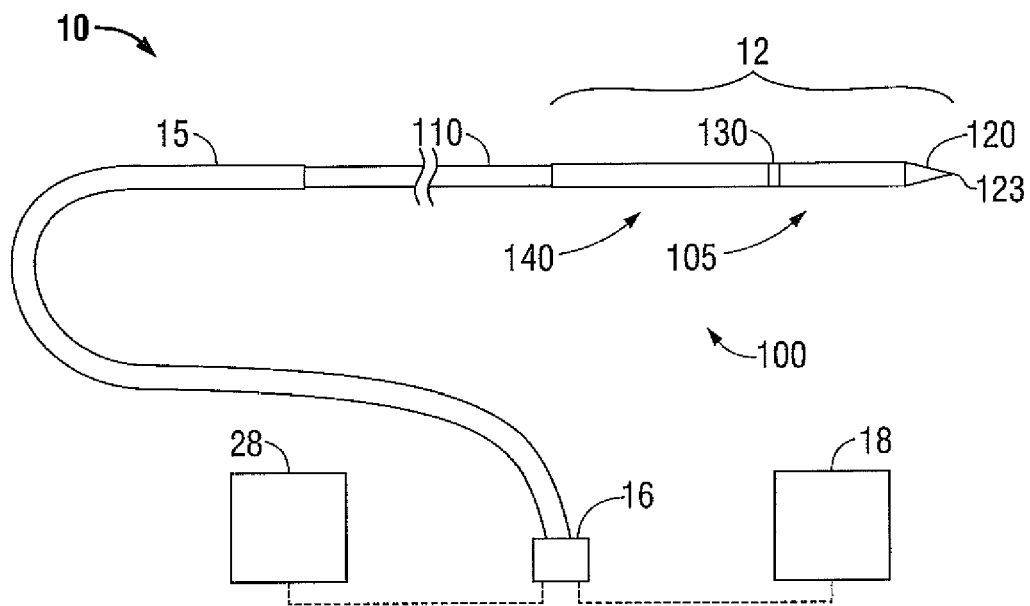
FIG. 1 is a schematic diagram of an ablation system according to an embodiment of the present disclosure.

Hereinafter, embodiments of the presently disclosed electrosurgical device with a directional radiation pattern will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is further from the user.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation assisted resection. As it is used in this description, "transmission line" generally refers to any transmission medium that can be used for the propagation of signals from one point to another.

Various embodiments of the present disclosure provide electrosurgical devices for treating tissue and methods of directing electromagnetic radiation to a target volume of tissue. Embodiments may be implemented using electromagnetic radiation at microwave frequencies or at other frequencies. An electrosurgical system including an energy applicator, according to various embodiments, is designed and configured to operate between about 500 MHz and about 10 GHz with a directional radiation pattern.

Various embodiments of the presently disclosed electrosurgical device with a directional radiation pattern are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

FIG. 1 shows an electrosurgical system 10, according to an embodiment of the present disclosure that includes an energy applicator or probe 100. Probe 100 generally includes an antenna assembly 12 having a radiating portion connected by a feedline 110 (or shaft) via a transmission line 15 to a connector 16, which may further operably connect the probe 100 to an electrosurgical power generating source 28, e.g., a microwave or RF electrosurgical generator.

Feedline 110 may be formed from a suitable flexible, semi-rigid or rigid microwave conductive cable and may connect directly to an electrosurgical power generating source 28. Alternatively, the feedline 110 may electrically connect the antenna assembly 12 via the transmission line 15 to the electrosurgical power generating source 28. Feedline 110 may have a variable length from a proximal end of the antenna assembly 12 to a distal end of transmission line 15 ranging from a length of about one inch to about twelve inches. Feedline 110 may be formed of suitable electrically conductive materials, e.g., copper, gold, silver or other conductive metals having similar conductivity values. Feedline 110 may be made of stainless steel, which generally offers the strength required to puncture tissue and/or skin. Conductive materials used to form the feedline 110 may be plated with other materials, e.g., other conductive materials, such as gold or silver, to improve their properties, e.g., to improve conductivity, decrease energy loss, etc. In some embodiments, the feedline 110 includes stainless steel, and to improve the conductivity thereof, the stainless steel may be coated with a layer of a conductive material such as copper or gold. Feedline 110 may include an inner conductor, a dielectric material coaxially surrounding the inner conductor, and an outer conductor coaxially surrounding the dielectric material. Antenna assembly 12 may be formed from a portion of the inner conductor that extends distal of the feedline 110 into the antenna assembly 12. Feedline 110 may be cooled by fluid e.g., saline or water, to improve power handling, and may include a stainless steel catheter.

In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. Transmission line 15 may additionally, or alternatively, provide a conduit (not shown) configured to provide coolant from a coolant source 18 to the probe 100.

Located at the distal end of the antenna assembly 12 is an end cap or tapered portion 120, which may terminate in a sharp tip 123 to allow for insertion into tissue with minimal resistance. The end cap or tapered portion 120 may include other shapes, such as, for example, a tip 123 that is rounded, flat, square, hexagonal, or cylindroconical.

In some variations, the antenna assembly 12 includes a distal radiating portion 105 and a proximal radiating portion 140. A junction member 130 may be provided. Junction member 130, or portions thereof may be disposed between the proximal and distal radiating portions, 140 and 105, respectively. In some embodiments, the distal and proximal radiating portions 105, 140 align at the junction member 130, which is generally made of a dielectric material, e.g., adhesives, and are also supported by the inner conductor that extends at least partially through the distal radiating portion 105. Junction member 130 may be formed from any suitable elastomeric or ceramic dielectric material by any suitable process. In some embodiments, the junction member 130 is formed by over-molding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. I. du Pont de Nemours and Company of Wilmington, Del., United States). Junction member 130 may be formed using any suitable over-molding compound by any suitable process, and may include use of a ceramic substrate.

In some embodiments, the antenna assembly 12 may be provided with a coolant chamber (not shown). Additionally, the junction member 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", now issued U.S. Pat. No. 8,118,808, and U.S. Pat. No. 7,311,703 entitled "DEVICES AND METHODS FOR COOLING MICROWAVE ANTENNAS".

In some embodiments, the antenna assembly 12 may be provided with an outer jacket (not shown) disposed about the distal radiating portion 105, the junction 130 and/or the proximal radiating portion 140. The outer jacket may be formed of any suitable material, such as, for example, polymeric or ceramic materials. The outer jacket may be applied by any suitable method, such as, for example, heat shrinking, over-molding, coating, spraying dipping, powder coating, baking and/or film deposition. The outer jacket may be a water-cooled catheter formed of a material having low electrical conductivity.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may provide ablations in short procedure times, e.g., a few minutes, to destroy cancerous cells in the target tissue region.

A plurality of probes 100 may be placed in variously-arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

In operation, microwave energy having a wavelength, lambda ($\lambda$), is transmitted through the antenna assembly 12, e.g., along the proximal and distal radiating portions 140, 105, and radiated into the surrounding medium, e.g., tissue. The length of the antenna for efficient radiation may be dependent on the effective wavelength $\lambda_{eff}$, which is dependent upon the dielectric properties of the medium being radiated. Antenna assembly 12 through which microwave energy is transmitted at a wavelength $\lambda$ may have differing effective wavelengths $\lambda_{eff}$ depending upon the surrounding medium, e.g., liver tissue as opposed to breast tissue.

Figure 2:
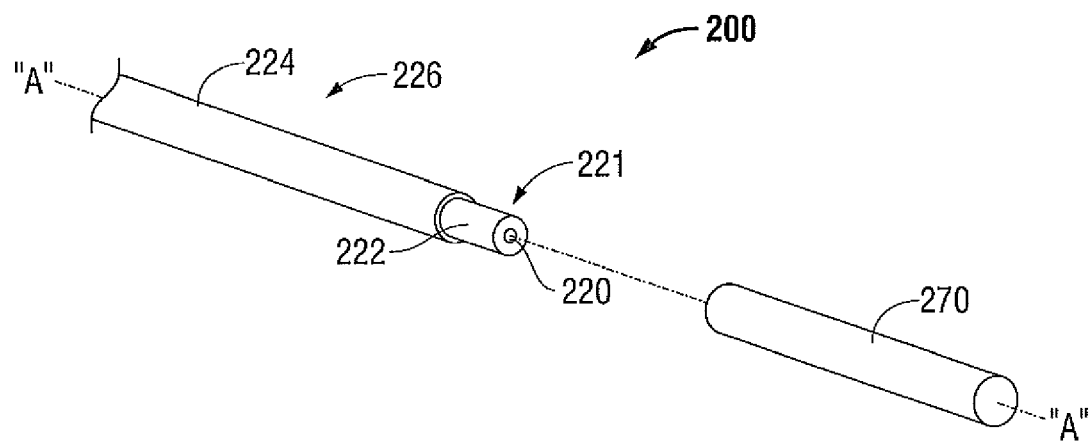
FIG. 2 is a perspective view with parts disassembled of a portion of an energy applicator according to an embodiment of the present disclosure.
Figure 15:
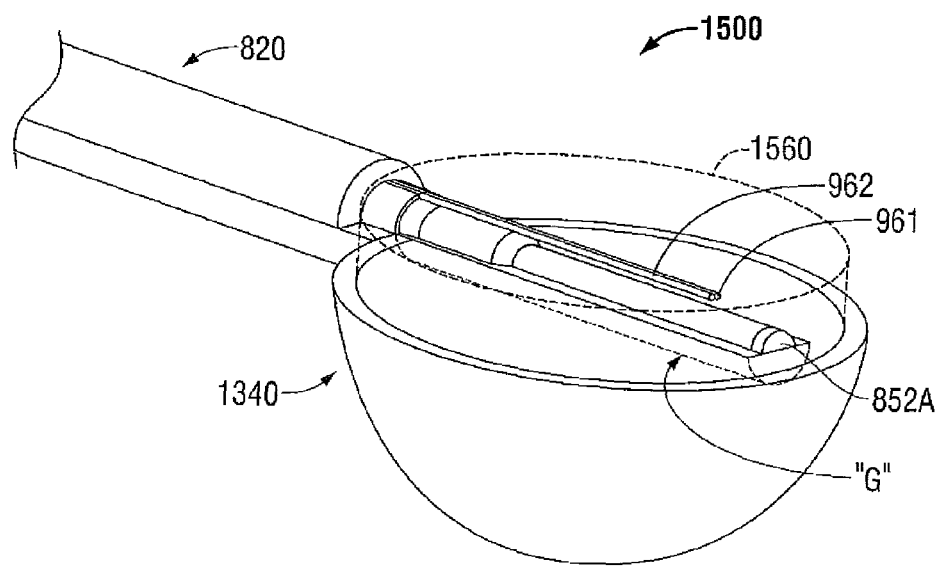
FIG. 15 is a perspective view of the portion of the energy applicator of FIG. 13 shown with a cooling chamber according to an embodiment of the present disclosure.
Figure 16:
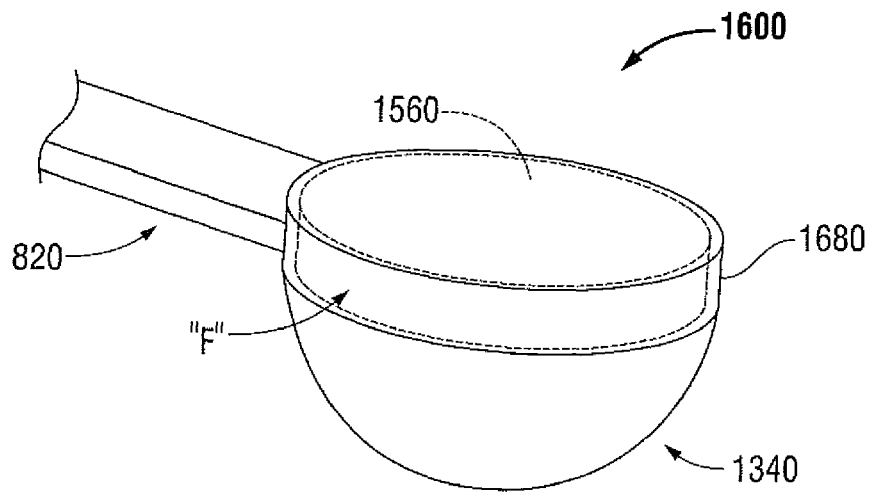
FIG. 16 is a perspective view of the portion of the energy applicator of FIG. 15 shown with a material disposed about the cooling chamber according to an embodiment of the present disclosure.

FIGS. 2 through 12, 15 and 16 show a sequentially-illustrated, assembly of components forming an energy applicator or probe, shown generally as 1600 in FIG. 16, in accordance with the present disclosure. In FIG. 2, a coaxial feedline 226 is shown with the outer conductor 224 trimmed back, such that a portion 221 of the dielectric material 222 and the inner conductor 220 extends beyond the outer conductor 224. According to an embodiment of the present disclosure, an energy applicator segment shown generally as 200 in FIG. 2 includes an electrically conductive element 270 that extends along the longitudinal axis "A" of the energy applicator segment 200. Electrically conductive element 270 may be positioned in a distal portion of the energy applicator 1600. In some embodiments, the electrically-conductive member 270 is a solid metal cylinder disposed at the distal end of the portion 221 electrically coupled to the inner conductor 220 (e.g., by solder). Electrically conductive element 270 may be formed of any suitable electrically-conductive material (e.g., metal such as stainless steel, aluminum, titanium, copper, etc.) of any suitable length. The shape and size of the electrically conductive element 270 may be varied from the configuration depicted in FIG. 2.

Figure 3:
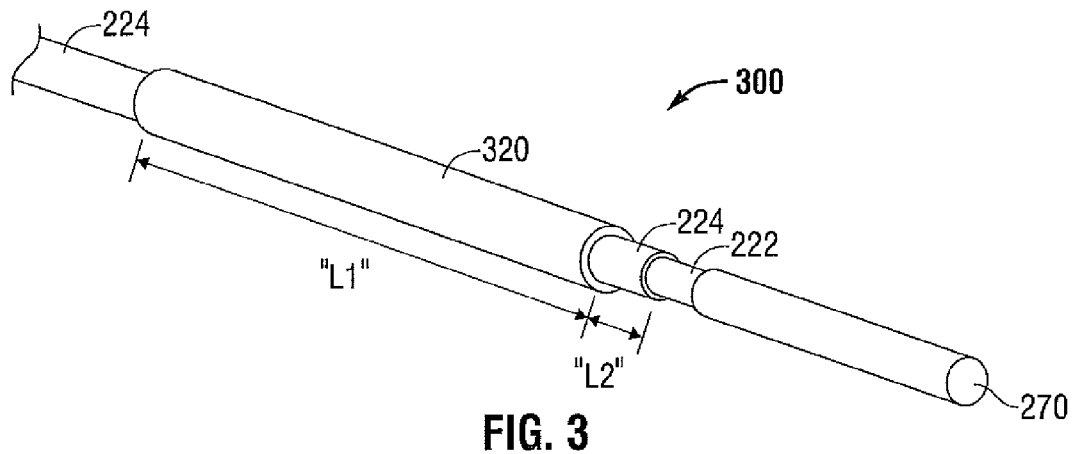
FIG. 3 is a perspective, assembled view of the portion of the energy applicator of FIG. 2 shown with a dielectric layer disposed about a portion of the outer conductor according to an embodiment of the present disclosure.

FIG. 3 shows an energy applicator segment 300 according to an embodiment of the present disclosure that is similar to the energy applicator segment 200 of FIG. 2, except for a dielectric layer 320 (also referred to herein as a balun insulator) disposed coaxially about a distal portion of the outer conductor 224 of the feedline 226. Dielectric layer 320 may have a suitable length "L1" in a range from about 0.1 inches to about 3.0 inches. Dielectric layer 320 may be spaced apart from and disposed proximal to the distal end of the outer conductor 224. In some embodiments, the dielectric layer 320 is spaced apart, by a length "L2", e.g., about 0.1 inches, from the distal end of the outer conductor 224. Balun insulator 320 may extend distally beyond the distal end of the conductive balun sleeve (e.g., 430 shown in FIG. 4) to direct current into a balancing/unbalancing (balun) structure (e.g., "B" shown in FIG. 4). Dielectric layer 320 may be formed of any suitable insulative material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, metal oxides or other suitable insulator, and may be formed in any suitable manner. Dielectric layer 320 may be grown, deposited or formed by any other suitable technique. In some embodiments, the balun insulator 320 is formed from a material with a dielectric constant in the range of about 1.7 to about 10. The shape, size and relative position of the balun insulator 320 may be varied from the configuration depicted in FIG. 3.

Figure 4:
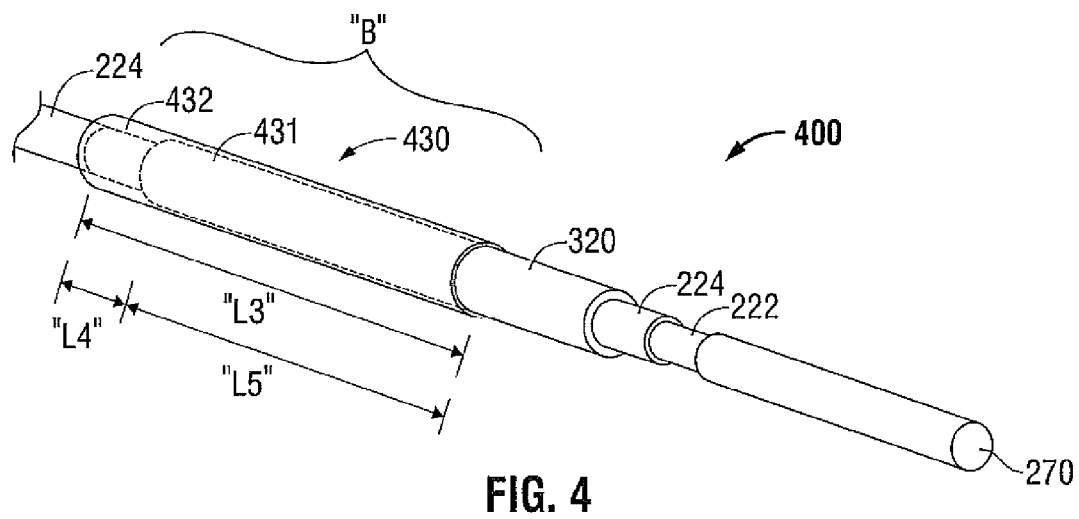
FIG. 4 is a perspective view of the portion of the energy applicator of FIG. 3 shown with an electrically-conductive layer disposed about a portion of the dielectric layer according to an embodiment of the present disclosure.

FIG. 4 shows an energy applicator segment 400 according to an embodiment of the present disclosure that is similar to the energy applicator segment 300 of FIG. 3 except for an electrically-conductive layer 430 (also referred to herein as a conductive balun sleeve) disposed coaxially about a proximal portion of the energy applicator segment 400. Electrically-conductive layer 430 may have any suitable length "L3", e.g., about 0.1 inches to about 3.0 inches. Electrically-conductive layer 430 may be formed as a single structure and electrically coupled to the outer conductor 224, e.g., by solder or other suitable electrical connection. In some embodiments, the electrically-conductive layer 430 includes a first portion 431, having a length "L5", disposed coaxially about a proximal portion of the dielectric layer 320, and a second portion 432, having a length "L4", disposed proximally to the first portion 431 electrically coupled to the outer conductor 224. First and second portions 431, 432 may be formed of any suitable electrically-conductive material, e.g., metal such as stainless steel, titanium, copper, etc., and may be formed in any suitable manner. First and second portions 431, 432 may be formed separately from each other. First and second portions 431, 432 may form a single, unitary structure. The shape and size of the electrically-conductive balun sleeve 430 may be varied from the configuration depicted in FIG. 4.

Figure 5:
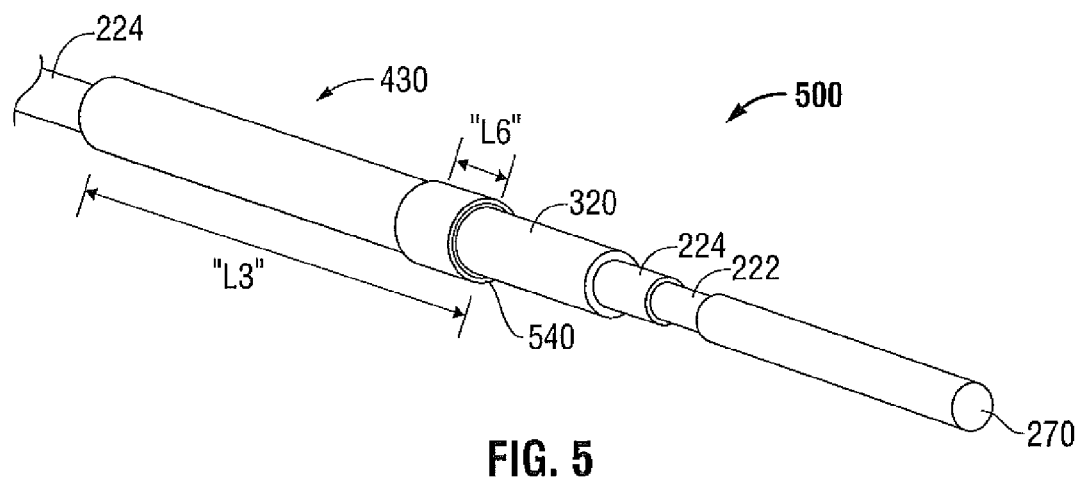
FIG. 5 is a perspective view of the portion of the energy applicator of FIG. 4 shown with an electrically-conductive cylinder disposed about the distal end of the electrically-conductive layer according to an embodiment of the present disclosure.

FIG. 5 shows an energy applicator segment 500 according to an embodiment of the present disclosure that is similar to the energy applicator segment 400 of FIG. 4, except for an electrically-conductive cylinder 540 disposed coaxially about a distal portion of the electrically-conductive layer 430. Electrically-conductive cylinder 540 may have a suitable length "L6" of a range from about 0.05 inches to about 0.2 inches. In some embodiments, the distal edge of electrically-conductive cylinder 540 is disposed overlying the distal edge of the electrically-conductive layer 430. The shape and size of the electrically-conductive cylinder 540 may be varied from the configuration depicted in FIG. 5.

Figure 6:
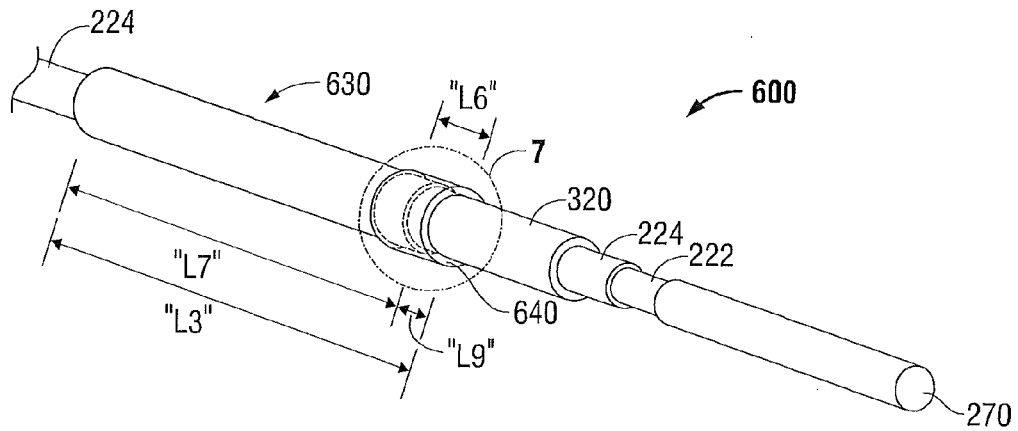
FIG. 6 is a perspective view of the portion of the energy applicator of FIG. 3 shown with another embodiment of an electrically-conductive layer and an electrically-conductive cylinder according to the present disclosure.

FIG. 6 shows an energy applicator segment 600 according to an embodiment of the present disclosure that includes an electrically-conductive layer 630 and an electrically-conductive cylinder 640. Electrically-conductive layer 630 surrounds a proximal portion of the dielectric layer 320 and is electrically coupled to the outer conductor 224, e.g., by solder or other suitable electrical connection. Electrically-conductive layer 630 is similar to the electrically-conductive layer 430 of FIG. 4, except that the electrically-conductive layer 630 has a length that is less than the length "L3" of the electrically-conductive layer 430. As shown in FIG. 6, the electrically-conductive layer 630 may have a length "L7", which is shorter than the length "L3" by a length "L9".

Figure 7:
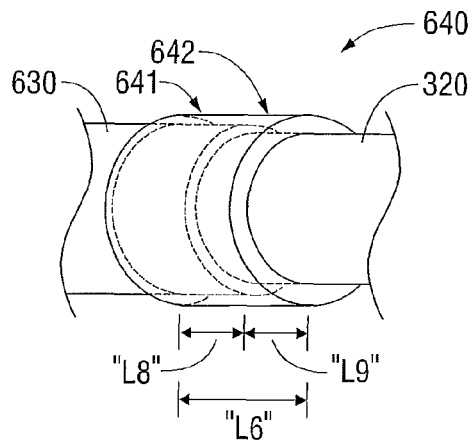
FIG. 7 is an enlarged view of the indicated area of detail of FIG. 6 according to an embodiment of the present disclosure.

Electrically-conductive cylinder 640 shown in FIGS. 6 and 7 is similar to the electrically-conductive cylinder 540 of FIG. 5, except that the electrically-conductive cylinder 640 extends distally beyond the distal edge of the electrically-conductive layer 630. As shown in FIG. 7, the electrically-conductive cylinder 640, having a length "L6", includes a first portion 641, having a length "L8", disposed coaxially about the distal end of the electrically-conductive layer 630, and a second portion 642, having a length "L9", disposed proximally to the first portion 641, surrounding a portion of the dielectric layer 320 distally extending beyond the electrically-conductive layer 630. In some embodiments, the electrically-conductive cylinder 640 is positioned relative to the distal edge of the electrically-conductive layer 630 such that the combined length of the electrically-conductive layer 630 and the electrically-conductive cylinder 640 is a length "L3", which may be, for example, a quarter wavelength or a half wavelength. The shape and size of the electrically-conductive cylinder 640 may be varied from the configuration depicted in FIGS. 6 and 7.

Figure 8:
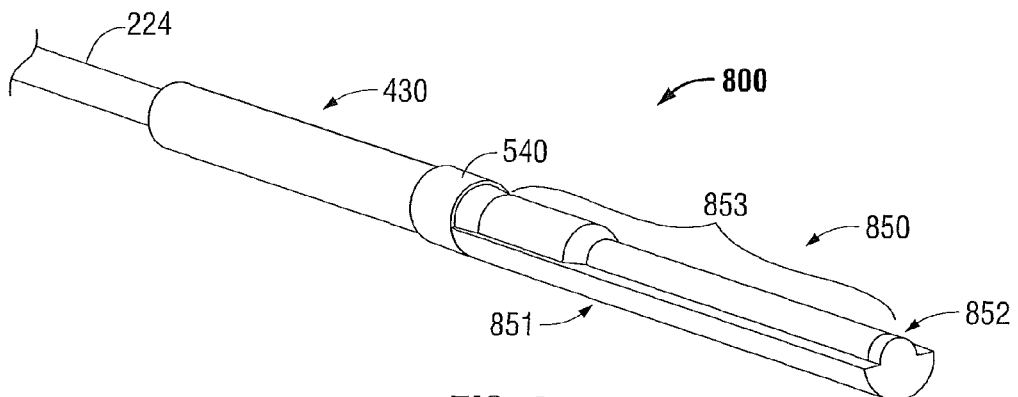
FIG. 8 is a perspective view of the portion of the energy applicator of FIG. 5 shown with a dielectric structure disposed distal to the electrically-conductive cylinder according to an embodiment of the present disclosure.

FIG. 8 shows an energy applicator segment 800 according to an embodiment of the present disclosure that is similar to the energy applicator segment 500 of FIG. 5, except for a generally longitudinally-disposed dielectric structure 850. In some embodiments, the dielectric structure 850 includes a dielectric cap configured to cover the distal end of the electrically-conductive member 270.

As shown in FIG. 8, the dielectric structure 850 may be disposed distally to the electrically-conductive cylinder 540. Dielectric structure 850 may be formed using over-molding techniques or other forming techniques. In some embodiments, the dielectric structure 850 is formed from a material with a dielectric constant in the range of about 1.7 to about 10. The shape and size of the dielectric structure 850 may be varied from the configuration depicted in FIG. 8.

In some embodiments, the dielectric structure 850 includes a first dielectric segment 851, a second dielectric segment 852, and a third dielectric segment 853. As shown in FIG. 8, the first dielectric segment 851 extends distally from the distal end of the electrically-conductive cylinder 540 and may have a substantially half-cylindrical shape. First dielectric segment 851 may be made to encompass any radial angle. In some embodiments, the first dielectric segment 851 extends from the distal end of the electrically-conductive cylinder 540 to distal end of the electrically-conductive member 270. Second dielectric segment 852 is configured to cover the distal end of the electrically-conductive member 270, and may include a first portion (e.g., 852A shown in FIG. 11) and a second portion (e.g., 852B shown in FIG. 11). In some embodiments, the first and second dielectric segments 851, 852 are integrally formed in a molding process. First dielectric segment 851, the second dielectric segment 852 and the third dielectric segment 853 may be formed by any suitable process.

Figure 9:
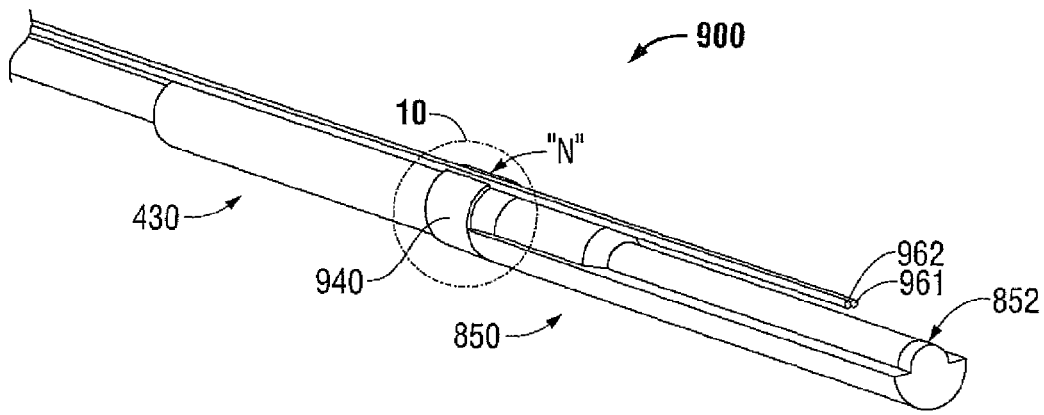
FIG. 9 is a perspective view of the portion of the energy applicator of FIG. 8 shown with a fluid inflow tube and a fluid outflow tube according to an embodiment of the present disclosure.

FIG. 9 shows an energy applicator segment 900 according to an embodiment of the present disclosure that is similar to the energy applicator segment 800 of FIG. 8, except for a longitudinally-extending inflow tube 961, a longitudinally-extending outflow tube 962, and an electrically-conductive cylinder 940 having a notch "N" defined therein that is configured to receive the inflow and outflow tubes 961, 962. In some embodiments, the inflow and outflow tubes 961, 962 are configured to supply and/or dispense coolant fluid (e.g., saline, water or other suitable coolant fluid) into and out of a distal portion of a cooling chamber (e.g., 1560 shown in FIG. 15). A pump (not shown) may be connected in fluid communication between the cooling chamber and a coolant source (e.g., 18 shown in FIG. 1). Inflow and outflow tubes 961, 962 may include thin-walled polyimide tubes. In some embodiments, a pump supplies coolant fluid from a coolant source to one or more inflow tubes 961 which, in turn, deliver coolant fluid to the cooling chamber (e.g., 1560 shown in FIG. 15). Additionally, or alternatively, a pump may be fluidly coupled to one or more outflow tubes 962 to draw coolant fluid out of the cooling chamber.

Figure 10:
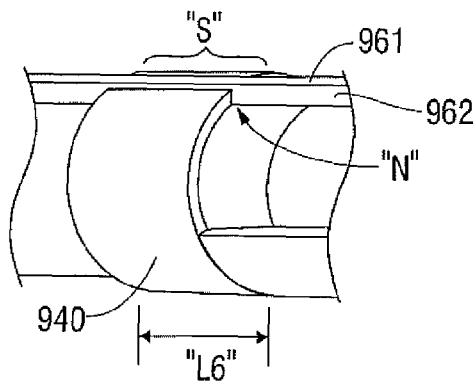
FIG. 10 is an enlarged view of the indicated area of detail of FIG. 9 according to an embodiment of the present disclosure.

As shown in FIGS. 9 and 10, the inflow and outflow tubes 961, 962 may extend longitudinally across the full length of the electrically-conductive layer 430 and at least partially across the dielectric structure 850. As shown in FIG. 10, a portion or segment "S" of the inflow and outflow tubes 961, 962 is disposed within a notch "N" defined within the electrically-conductive cylinder 940. In some embodiments, the notch "N" is configured as a recess, e.g., in the form of a groove or hole. In other embodiments, the notch "N" is configured as a first recess (not shown) and a second recess (not shown), wherein the first recess is configured to receive one or more inflow tubes 961 and the second recess is configured to receive one or more outflow tubes 962.

Inflow tube 961 and the outflow tube 962 may be formed to have the same diameters or different diameters. Inflow and outflow tubes 961, 962 may have any suitable length. In some embodiments, the segment "S" of the inflow and outflow tubes 961, 962 is disposed between the electrically-conductive layer 430 and the outer circumferential surface of the electrically-conductive cylinder 940, which helps minimize the outer diameter of the device. Inflow and outflow tubes 961, 962 may be held in place, e.g., along the electrically-conductive layer 430 and/or within the notch "N", by using UV adhesive or other similar suitable adhesives, as well as heat shrink tubing or by other suitable methods. The shape and size of the inflow and outflow tubes 961, 962, the electrically-conductive cylinder 940 and the notch "N" may be varied from the configurations depicted in FIGS. 9 and 10.

Figure 11:
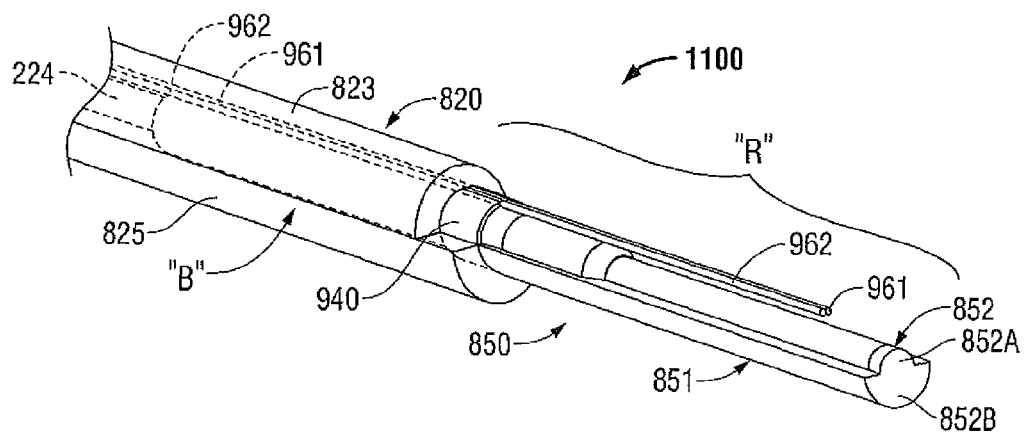
FIG. 11 is a perspective view of the portion of the energy applicator of FIG. 9 shown with a handle assembly disposed proximal to the proximal end of the dielectric structure according to an embodiment of the present disclosure.
Figure 14:
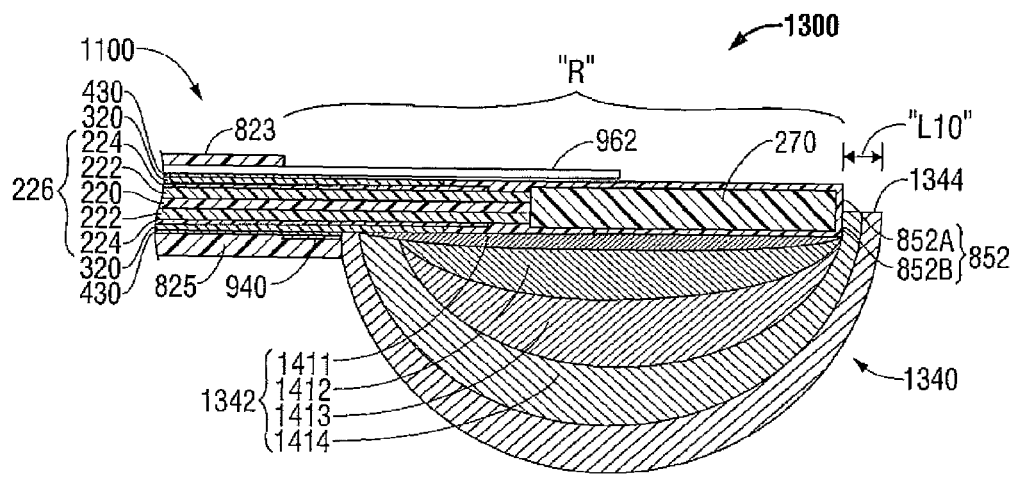
FIG. 14 is a cross-sectional view of the energy applicator of FIG. 13 according to an embodiment of the present disclosure.

FIG. 11 shows an energy applicator segment 1100 according to an embodiment of the present disclosure that is similar to the energy applicator segment 900 of FIG. 9, except for a handle assembly 820 disposed proximal to the dielectric structure 850. A distal portion of the handle assembly 820 overlies at least a portion of the balun structure "B". Additionally, or alternatively, the handle assembly 820 is coaxially disposed around at least a portion of the outer conductor 224 of the feedline. A longitudinal cross-sectional view of the energy applicator segment 1100 is shown in FIG. 14.

As shown in FIG. 11, the handle assembly 820 may include a first portion 823 and a second portion 825. In some embodiments, the first portion 823 has a substantially half-cylindrical shape, and the second portion 825 has a substantially half-cylindrical shape. In some embodiments, the first portion 823 of the handle assembly 820 is disposed proximal to the electrically-conductive cylinder 940, whereby proximal portions of the inflow and outflow tubes 961, 962 disposed proximal to the electrically-conductive cylinder 940 are covered by the first portion 823. Energy applicator segment 1100 includes a radiating portion (shown generally as "R" in FIG. 11) that extends distally beyond the distal end of the handle assembly 820 or portion thereof (e.g., first portion 823) for radiating electromagnetic energy in a variety of possible directional radiation patterns.

Figure 12:
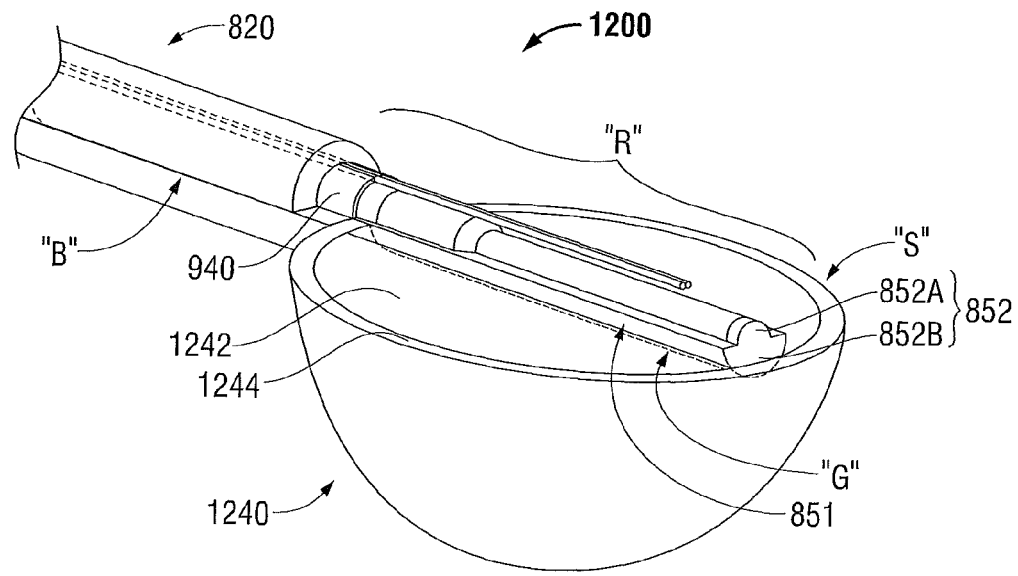
FIG. 12 is a perspective view of the portion of the energy applicator of FIG. 11 shown with a shell assembly disposed distal to the distal end of the handle assembly according to an embodiment of the present disclosure.

FIG. 12 shows an energy applicator segment 1200 according to an embodiment of the present disclosure that is similar to the energy applicator segment 1100 of FIG. 11, except for a shell assembly 1240 disposed distal to the distal end of the handle assembly 820. In some embodiments, the shell assembly 1240 extends distally beyond the length of the radiating portion "R". In some embodiments, the shell assembly 1240 has a substantially half-spherical shape. Shell assembly 1240 may be electrically coupled to the distal end of the conductive balun sleeve 430 of the balun structure "B".

Shell assembly 1240 may be shaped in such a manner to provide a desired surface ablation shape as well as aid in impedance matching. For example, the shell assembly 1240 may taper from a diameter similar to the diameter of the balun structure "B" to a larger diameter as the shell assembly 1240 extends proximally. Shell assembly 1240 may have any suitable shape and may be designed for tight spaces encountered during surgical operations. For example, the shell assembly 1240 may have a shape similar to the shape of a thick butter knife (e.g., 1740 shown in FIG. 17) or a half-cylindrical shape (e.g., 1940 shown in FIG. 19).

As shown in FIG. 12, the shell assembly 1240 may include an outer portion 1244 and an inner portion 1242. Shell assembly 1240 may be configured such that a portion of the radiating portion "R" is disposed substantially adjacent to the outer portion 1244. For example, the shell assembly 1240 may be configured such that a portion of the second portion 852B of the cap of dielectric material 852 at the distal end of the radiating portion "R" is disposed substantially adjacent to the outer portion 1244. In some embodiments, a portion of the cap of dielectric material 852 and a portion of the first dielectric segment 851 are disposed in a recess in the form of a groove "G" defined in the planar top surface "S" of the inner portion 1242.

Outer portion 1244 may include an electrically conductive material, such as, for example, copper, stainless steel, titanium, titanium alloys such as nickel-titanium and titanium-aluminum-vanadium alloys, aluminum, aluminum alloys, tungsten carbide alloys or combinations thereof. Portions of the outer portion 1244 may be loaded with low- to mid-range permittivity dielectric materials to aid in radiation directivity and impedance matching. In general, the dielectric permittivity would increase in value with radial distance from the electrically-conductive member 270. Several shells, or other shapes, of different dielectric materials may nest together to form the outer portion 1244.

Inner portion 1242 may include a dielectric material. In some embodiments, the inner portion 1242 includes dielectric material layers. For example, the inner portion 1242 may include one or more thin layers, one or more thick layers or a mixture of thick and thin layers. Inner portion 1242 may be composed of any suitable dielectric material which may be the same as, or different from, the dielectric material, if any, used in the outer portion 1244. The dielectric materials used to form the inner portion 1242 may vary in dielectric constant with shells (e.g., 1411, 1412, 1413 and 1414 shown in FIG. 14) or more complex dielectric layering to achieve the optimum antenna directivity and energy to tissue delivery.

Figure 13:
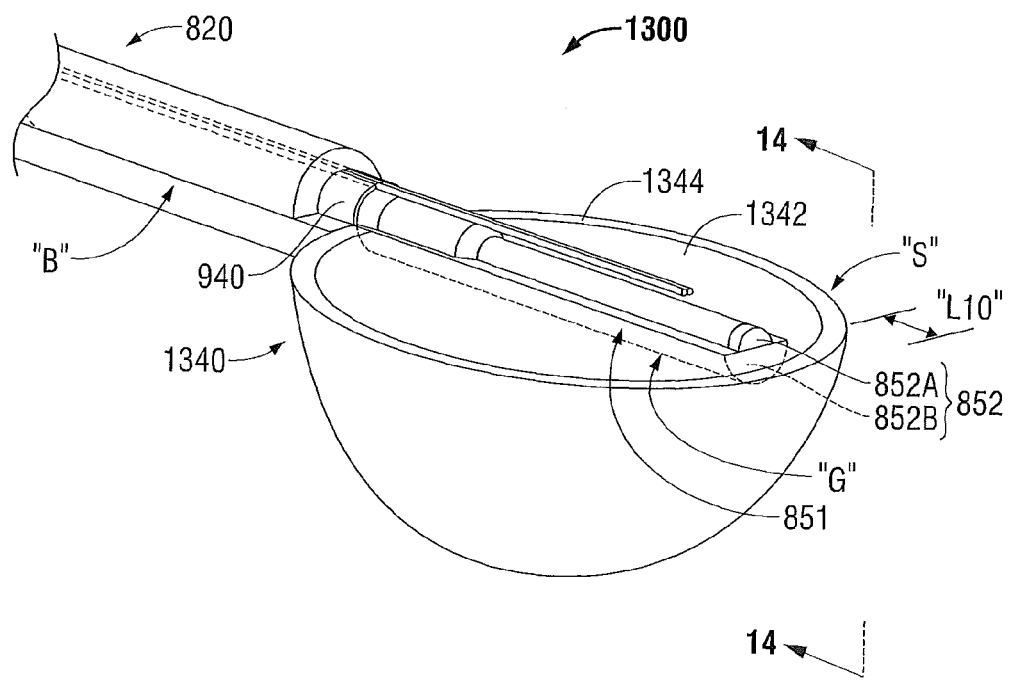
FIG. 13 is a perspective view of the portion of the energy applicator of FIG. 11 shown with another embodiment of a shell assembly disposed distal to the distal end of the handle assembly according to the present disclosure.

FIG. 13 shows an energy applicator segment 1300 according to an embodiment of the present disclosure that is similar to the energy applicator segment 1100 of FIG. 11, except for a shell assembly 1340 disposed distal to the distal end of the handle assembly 820 according to another embodiment the present disclosure. Shell assembly 1340 includes an outer portion 1344 and an inner portion 1342. In some embodiments, the outer portion 1344 of the shell assembly 1340 is formed of an electrically conductive material e.g., stainless steel, and electrically coupled to the distal end of the conductive balun sleeve 430 of the balun structure "B". Inner portion 1342 of the shell assembly 1340 may be formed of any suitable dielectric material. A distal portion of the inner portion 1342 (e.g., 1414 shown in FIG. 14) may extend distal to the radiating portion "R".

As shown in FIG. 13, the inner portion 1342 may include a flat planar surface "S" having a recess in the form of a groove "G" defined therein. Groove "G" is configured to receive at least a portion of the radiating portion "R". In some embodiments, the groove "G" is configured to receive the second portion 852B of the cap of dielectric material 852 and the first dielectric segment 851 of the dielectric structure 850.

FIG. 14 is a cross-sectional view of the energy applicator segment 1300 of FIG. 13 according to an embodiment of the present disclosure. As shown in FIG. 14, the inner portion 1342 of the shell assembly 1340 may be formed of a first dielectric layer 1411, a second dielectric layer 1412, a third dielectric layer 1413 and a fourth dielectric layer 1414. Inner portion 1342 may include any suitable number of dielectric layers in varied configurations. A variety of dielectric materials may suitably be used, including, but not limited to, polymers, ceramics, metal oxides and combinations thereof.

As shown in FIG. 14, the fourth dielectric layer 1414 is disposed adjacent to the outer portion 1344 of the shell assembly 1340, and a distal portion of the fourth dielectric layer 1414 may be disposed distal to the distal end of the radiating portion "R". The shape and size of the first dielectric layer 1411, the second dielectric layer 1412, the third dielectric layer 1413 and the fourth dielectric layer 1414 may be varied from the configuration depicted in FIG. 14.

FIG. 15 shows an energy applicator segment 1500 according to an embodiment of the present disclosure that is similar to the energy applicator segment 1300 of FIG. 13, except for a chamber 1560 (also referred to herein as a cooling chamber). In some embodiments, portions of the inflow and outflow tubes 961, 962 are disposed within the chamber 1560. In some embodiments, the inflow and outflow tubes 961, 962 are configured to supply coolant fluid "F" (e.g., saline, water or other suitable coolant fluid) into and out of a distal portion of the cooling chamber 1560. Additionally, or alternatively, the chamber 1560 may include a material having a high dielectric constant, such as alumina, titanium dioxide or zirconium dioxide, for improved antenna directivity and energy to tissue delivery efficiency. The shape and size of the inflow and outflow tubes 961, 962 and the chamber 1560 may be varied from the configuration depicted in FIG. 15.

FIG. 16 shows an energy applicator 1600 according to an embodiment of the present disclosure that includes the energy applicator segment 1500 of FIG. 15 shown with a material 1680 disposed about the cooling chamber 1560. Material 1680 may include any suitable material. Suitable materials for use as the material 1680 may include high dielectric-constant materials, such as, for example, inorganic nonmetallic materials (e.g., ceramics), metallic oxides (e.g., alumina, titanium dioxide, zirconium dioxide, or zinc oxide) and combinations thereof. Material 1680 may include a nonconductive radio frequency transparent material, e.g., a glass fiber epoxy composite polyimide, high temperature conformable rubber or plastic. Material 1680 may be formed using over-molding techniques or other forming techniques.

The outer surface of the energy applicator 1600 may be coated with a suitable lubricious substance, such as TEFLON®, to aid in the movement of the energy applicator 1600 in or through tissue as well as to aid in preventing tissue from sticking to the outer surface of the device.

Energy applicator 1600 may be rotatable about a longitudinal axis "A-A" (shown in FIG. 2) such that the directional radiation pattern "R" rotates therewith. Examples of antenna assemblies rotatable about axis "A-A" such that any elongated radiation lobes rotates therewith are disclosed in commonly assigned U.S. patent application Ser. No. 12/197,405 filed on Aug. 25, 2008, entitled "MICROWAVE ANTENNA ASSEMBLY HAVING A DIELECTRIC BODY PORTION WITH RADIAL PARTITIONS OF DIELECTRIC MATERIAL".

Figure 17:
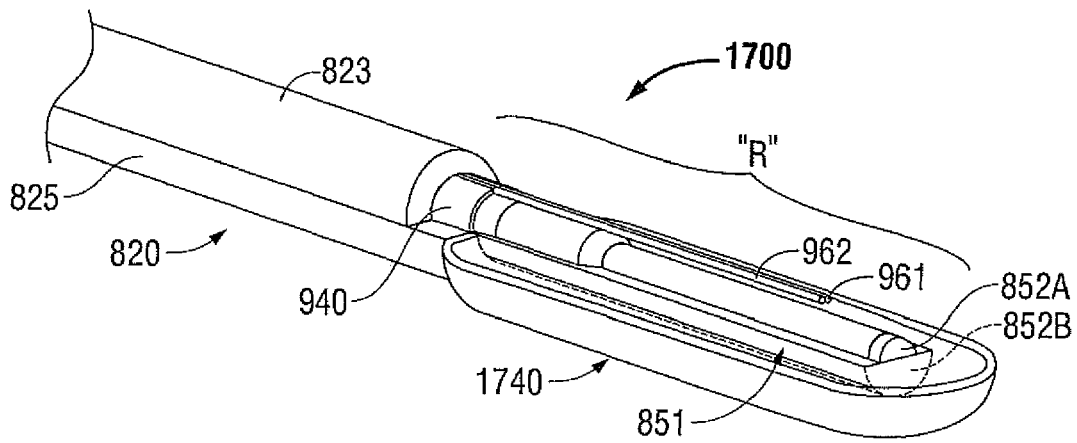
FIG. 17 is a perspective view of the portion of the energy applicator of FIG. 11 shown with yet another embodiment of a shell assembly disposed distal to the distal end of the handle assembly according to the present disclosure.

FIG. 17 shows an energy applicator segment 1700 according to an embodiment of the present disclosure that is similar to the energy applicator segment 1300 of FIG. 13, except for a shell assembly 1740 disposed distal to the distal end of the handle assembly 820. In FIG. 17, the shell assembly 1740 has a shape similar to the shape of a thick butter knife and may be suitable for tight spaces encountered during surgical operations. Shell assembly 1740 is similar, except for shape, to the shell assembly 1340 shown in FIG. 13, and further description thereof is omitted in the interests of brevity.

Figure 18:
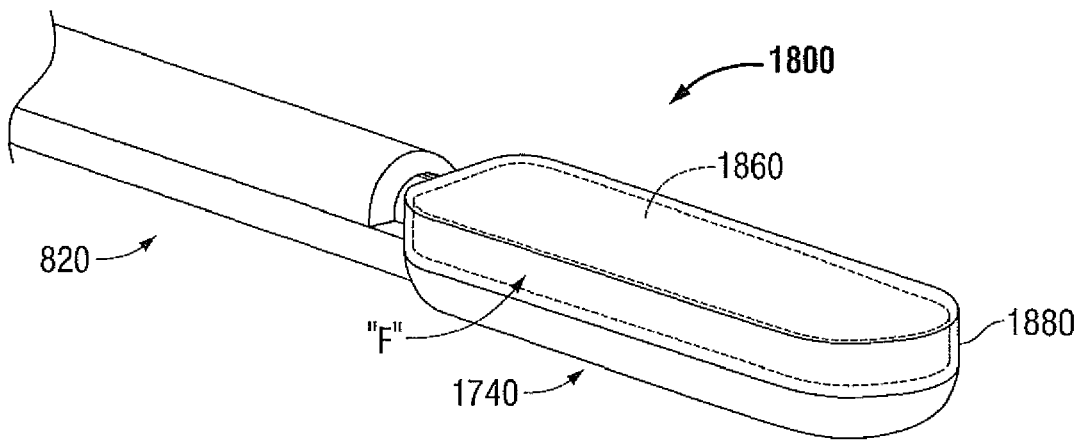
FIG. 18 is a perspective view of the portion of the energy applicator of FIG. 17 shown with a cooling chamber and a material disposed thereabout according to an embodiment of the present disclosure.

FIG. 18 shows an energy applicator 1800 according to an embodiment of the present disclosure that includes the energy applicator segment 1700 of FIG. 17 shown with a chamber (also referred to herein as a cooling chamber) 1860 and a material 1880 disposed thereabout. In some embodiments, portions of the inflow and outflow tubes 961, 962 are disposed within the chamber 1860. In some embodiments, the inflow and outflow tubes 961, 962 are configured to supply and/or dispense coolant fluid "F" (e.g., saline, water or other suitable coolant fluid) into and out of a distal portion of the cooling chamber 1860. Chamber 1860 and the material 1880 disposed thereabout are similar, except for shape, to the chamber 1560 and the material 1680 shown in FIGS. 15 and 16, respectively, and further description thereof is omitted in the interests of brevity.

Figure 19:
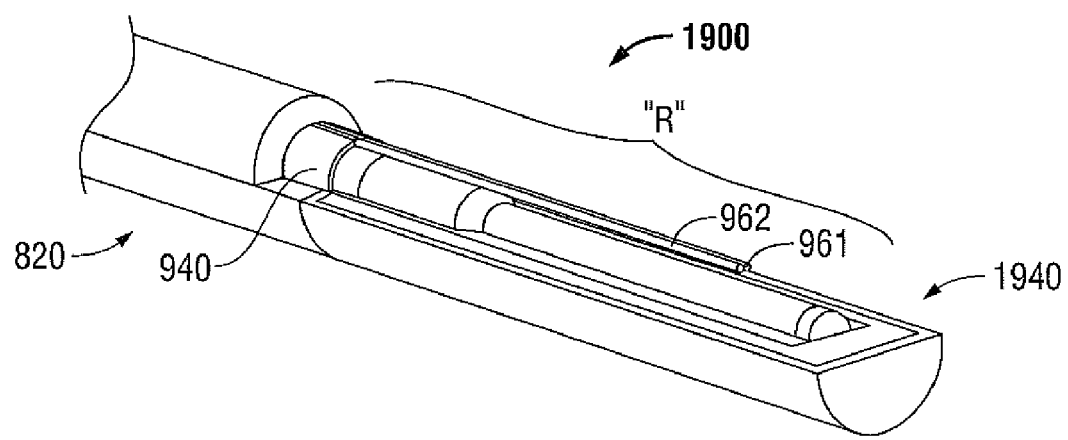
FIG. 19 is a perspective view of the portion of the energy applicator of FIG. 11 shown with still another embodiment of a shell assembly disposed distal to the distal end of the handle assembly according to the present disclosure.

FIG. 19 shows an energy applicator segment 1900 according to an embodiment of the present disclosure that is similar to the energy applicator segment 1300 of FIG. 13, except for a shell assembly 1940 disposed distal to the distal end of the handle assembly 820. In FIG. 19, the shell assembly 1940 has a substantially half-cylindrical shape and may be suitable for tight spaces encountered during surgical operations. Shell assembly 1940 is similar, except for shape, to the shell assembly 1340 shown in FIG. 13, and further description thereof is omitted in the interests of brevity.

Figure 20:
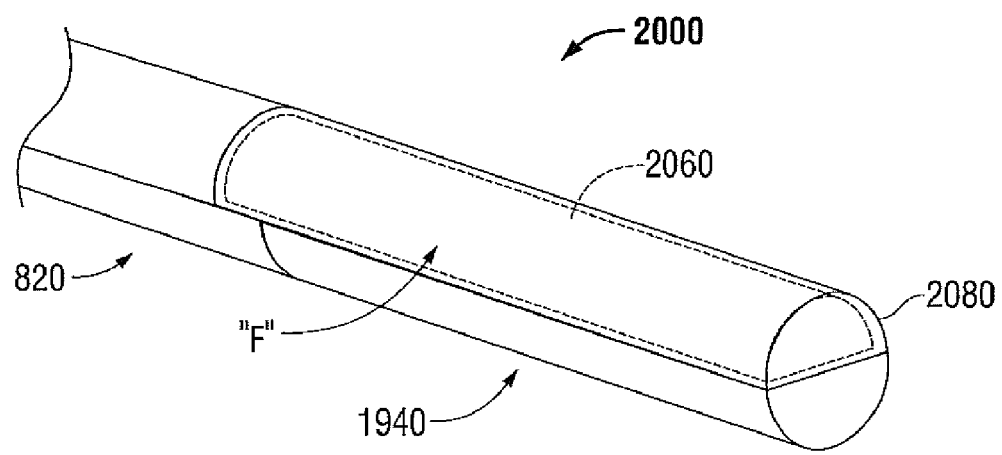
FIG. 20 is a perspective view of the portion of the energy applicator of FIG. 19 shown with a cooling chamber and a material disposed thereabout according to an embodiment of the present disclosure.

FIG. 20 shows an energy applicator 2000 according to an embodiment of the present disclosure that includes the energy applicator segment 1900 of FIG. 19 shown with a chamber (also referred to herein as a cooling chamber) 2060 and a material 2080 disposed thereabout. In some embodiments, portions of the inflow and outflow tubes 961, 962 are disposed within the chamber 2060. In some embodiments, the inflow and outflow tubes 961, 962 are configured to supply and/or dispense coolant fluid "F" (e.g., saline, water or other suitable coolant fluid) into and out of a distal portion of the cooling chamber 2060. Chamber 2060 and the material 2080 disposed thereabout are similar, except for shape, to the chamber 1560 and the material 1680 shown in FIGS. 15 and 16, respectively, and further description thereof is omitted in the interests of brevity.

Figure 21:
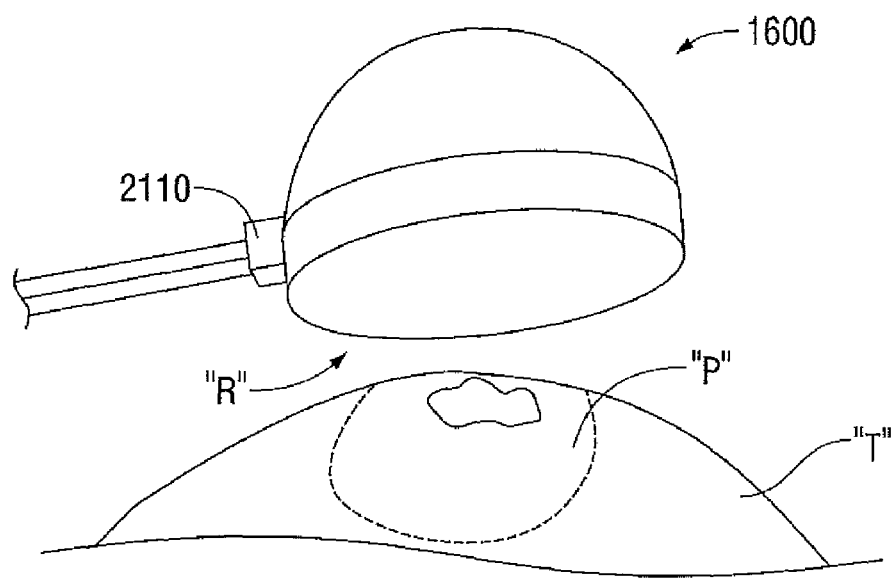
FIG. 21 is a diagrammatic representation of a radiation pattern of electromagnetic energy delivered into tissue by an energy applicator, such as the energy applicator of FIG. 16, according to an embodiment of the present disclosure.

FIG. 21 is a diagrammatic representation of a radiation pattern "P" of electromagnetic energy delivered into tissue "T" by the radiating portion "R" of an energy applicator, such as the energy applicator 1600 of FIG. 16, according to an embodiment of the present disclosure. A flexible joint 2110, e.g., a ball joint, conformable shaft or pivot joint may be employed at the proximal side of the radiating portion "R" to ease placement of the energy applicator in direct contact with the surface tissue "T". Radio frequency transparent materials in contact with the tissue may be made conformal to mate uninterruptedly with the surface tissue "T". This may include the use of a water bolus or other high dielectric fluid within a radio frequency transparent balloon.

Figure 22:
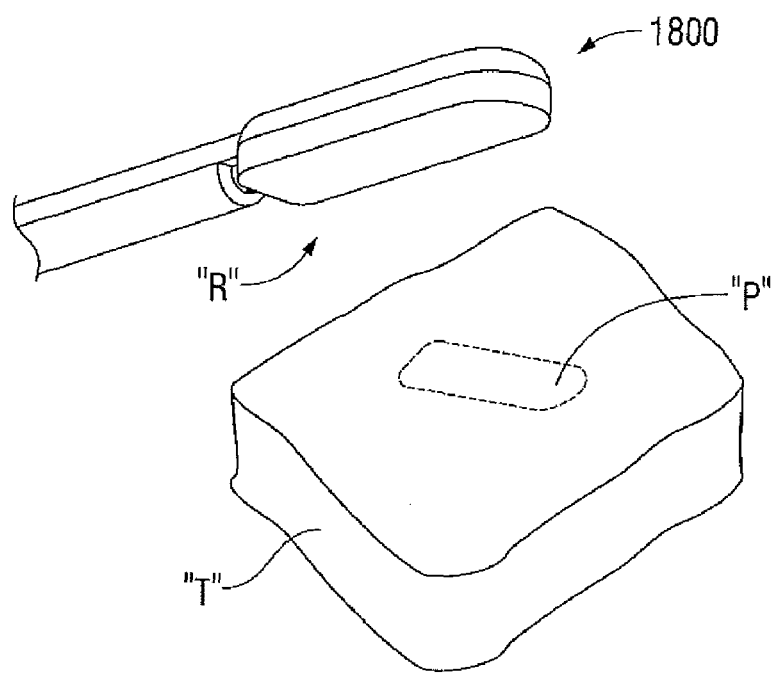
FIG. 22 is a diagrammatic representation of a radiation pattern of electromagnetic energy delivered into tissue by an energy applicator, such as the energy applicator of FIG. 18, according to an embodiment of the present disclosure.

FIG. 22 is a diagrammatic representation of a radiation pattern "P" of electromagnetic energy delivered into tissue "T" by the radiating portion "R" of an energy applicator, such as the energy applicator 1800 of FIG. 18, according to another embodiment of the present disclosure. The energy applicator may be made compatible to laparoscopic procedures whereby the shaft is conformable and controlled by a doctor proximally from the radiating portion "R". The radiating portion "R" may be made rotatable as well for laparoscopic applications.

Hereinafter, a method of manufacturing an energy applicator or probe having a dielectric loaded coaxial aperture with distally positioned resonant structure, in accordance with the present disclosure, is described with reference to FIG. 23. It is to be understood that the steps of the method provided herein may be performed in combination and in a different order than presented herein without departing from the scope of the disclosure.

Figure 23:
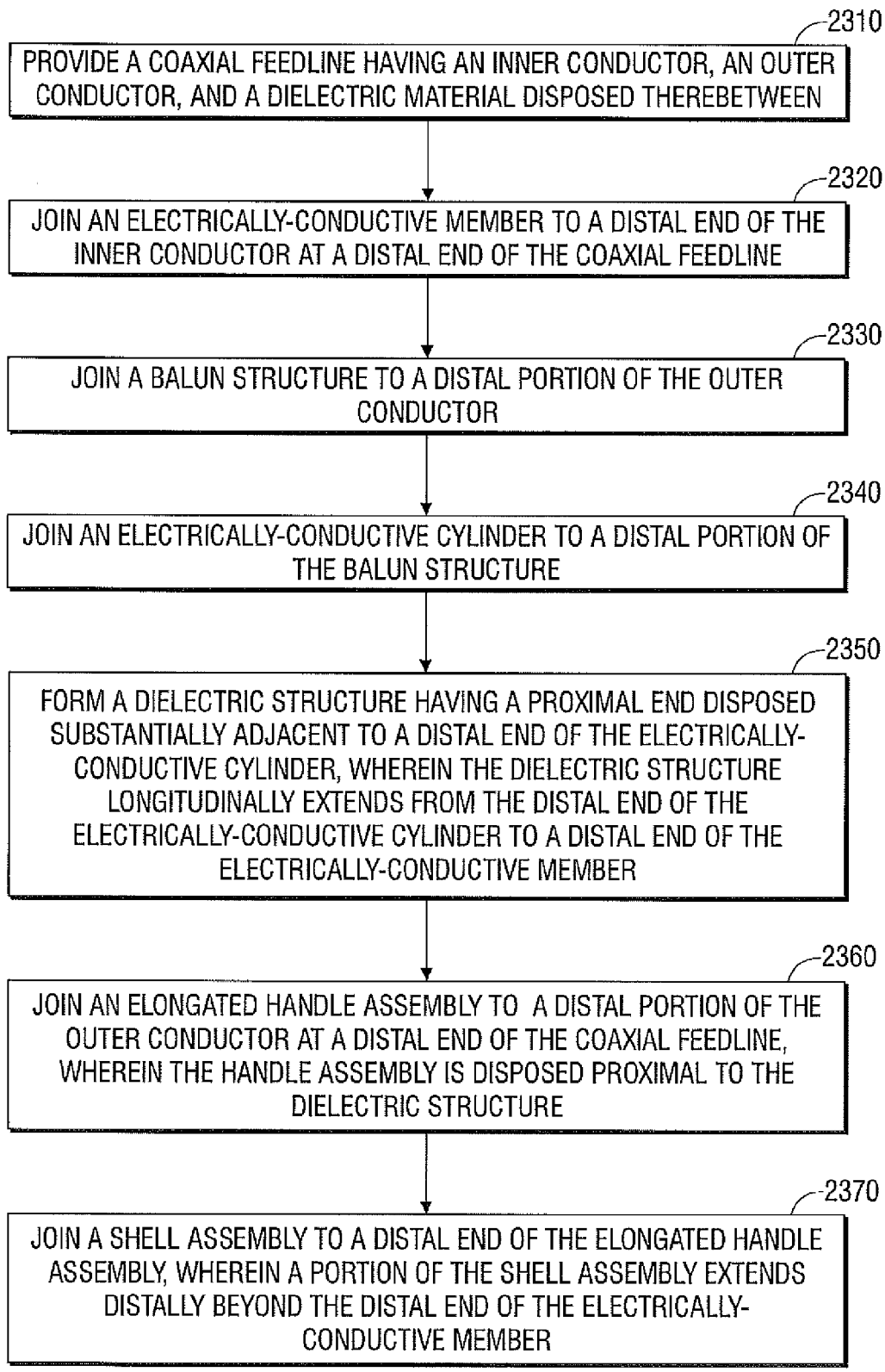
FIG. 23 is a flowchart illustrating a method of manufacturing an electrosurgical device according to an embodiment of the present disclosure.

FIG. 23 is a flowchart illustrating a method of manufacturing an electrosurgical device according to an embodiment of the present disclosure. In step 2310, a coaxial feedline (e.g., 226 shown in FIG. 2) is provided. The coaxial feedline includes an inner conductor (e.g., 220 shown in FIG. 2), an outer conductor (e.g., 224 shown in FIG. 2) and a dielectric material (e.g., 222 shown in FIG. 2) disposed therebetween. A portion of the inner conductor and the dielectric material (e.g., 221 shown in FIG. 2) may extend beyond the outer conductor at the distal end of the coaxial feed line.

In step 2320, an elongated electrically-conductive member (e.g., 270 shown in FIG. 2) is joined to the distal end of the inner conductor (e.g., 220 shown in FIG. 2) at a distal end of the coaxial feedline. In some embodiments, the electrically-conductive member is a solid metal cylinder electrically coupled to the inner conductor, e.g., by solder or other suitable electrical connection.

In step 2330, a balun structure (e.g., "B" shown in FIG. 4) is joined to a distal portion of the outer conductor (e.g., 224 shown in FIG. 3). The balun structure may be a quarter wavelength sleeve balun. In some embodiments, the balun structure includes a balun insulator (e.g., 320 shown in FIG. 3) coaxially disposed around a distal portion of the outer conductor, and an electrically-conductive balun sleeve (e.g., 430 shown in FIG. 4) coaxially disposed around a proximal portion of the balun insulator, wherein the conductive balun sleeve is electrically coupled to the outer conductor. The balun insulator may extend distally beyond the distal end of the electrically-conductive balun sleeve to direct currents into the balun.

In step 2340, an electrically-conductive cylinder (e.g., 540 shown in FIG. 5) is positioned overlying a distal portion of the balun structure. In some embodiments, a portion (e.g., 642 shown in FIG. 7) of the electrically-conductive cylinder (e.g., 640 shown in FIGS. 6 and 7) extends distally beyond the distal edge of an electrically-conductive balun sleeve (e.g., 630 shown in FIG. 7) of the balun. In some embodiments, the electrically-conductive cylinder is positioned relative to the distal edge of the electrically-conductive balun sleeve such that the combined length of the conductive balun sleeve and the conductive cylinder is a quarter wavelength or a half wavelength.

In step 2350, a dielectric structure (e.g., 850 shown in FIG. 8) is formed having a proximal end disposed substantially adjacent to a distal end of the electrically-conductive cylinder, wherein the dielectric structure longitudinally extends from the distal end of the electrically-conductive cylinder to a distal end of the electrically-conductive member. In some embodiments, the dielectric structure includes a cap of dielectric material (e.g., 852 shown in FIG. 8) configured to cover the distal end of the electrically-conductive member. The dielectric structure may be formed using over-molding techniques or other forming techniques.

In step 2360, an elongated handle assembly (e.g., 820 shown in FIG. 11) is joined to the outer conductor at a distal end of the coaxial feedline, wherein the handle assembly is disposed proximal to the dielectric structure. In some embodiments, a distal portion of the elongated handle assembly overlies at least a portion of the balun structure (e.g., "B" shown in FIG. 11).

In step 2370, a shell assembly (e.g., 1240 shown in FIG. 12) is joined to a distal end of the elongated handle assembly (e.g., 820 shown in FIG. 12), wherein a portion of the shell assembly (e.g., 1244 shown in FIG. 12) extends distally beyond the distal end of the electrically-conductive member.

The above-described electrosurgical devices for treating tissue and methods of directing electromagnetic radiation to a target volume of tissue may be used to provide directional microwave ablation, wherein the heating zone may be focused to one side of the electrosurgical device, thereby allowing clinicians to target small and/or hard to reach tumors without having to penetrate the tumor directly or kill more healthy tissue than necessary. The presently disclosed electrosurgical devices may allow clinicians to avoid ablating critical structures, such as large vessels, healthy organs or vital membrane barriers, by placing the electrosurgical device between the tumor and critical structure and directing the electromagnetic radiation toward the tumor and away from the critical structure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical device for directing energy to a target volume of tissue, comprising:
   a coaxial feedline having an inner conductor, an outer conductor coaxially disposed around the inner conductor, and a dielectric material disposed therebetween;
   an elongated electrically-conductive member longitudinally disposed at a distal end of the inner conductor;
   a balun including:
      a dielectric layer coaxially disposed around a distal portion of the outer conductor; and
      an electrically-conductive layer coaxially disposed around a proximal portion of the dielectric layer;
   an electrically-conductive cylinder coaxially disposed around a distal portion of the electrically-conductive layer of the balun;
   a dielectric structure disposed substantially adjacent to a distal end of the electrically-conductive cylinder, wherein the dielectric structure longitudinally extends from the distal end of the electrically-conductive cylinder to a distal end of the electrically-conductive member;
   an elongated handle assembly coaxially disposed around a portion of the outer conductor at a distal end of the coaxial feedline, wherein the handle assembly is disposed proximal to the dielectric structure; and
   a shell assembly disposed at a distal end of the elongated handle assembly, wherein the shell assembly is coupled to a distal portion of the balun.

2. The electrosurgical device of claim 1, wherein a portion of the inner conductor and the dielectric material of the coaxial feedline extends beyond the outer conductor at a distal end of the coaxial feedline.

3. The electrosurgical device of claim 1, wherein the electrically-conductive member is electrically coupled to the inner conductor.

4. The electrosurgical device of claim 1, wherein the balun is a quarter wavelength sleeve.

5. The electrosurgical device of claim 1, wherein the electrically-conductive layer includes a first portion coaxially disposed around the proximal portion of the dielectric layer, and a second portion disposed proximally to the first portion, the second portion electrically coupled to the outer conductor.

6. The electrosurgical device of claim 1, wherein the dielectric structure is configured to cover a distal end of the electrically-conductive member.

7. The electrosurgical device of claim 1, further comprising:
   a cooling chamber disposed at least partially about the electrically-conductive member.

8. The electrosurgical device of claim 7, further comprising:
   an inflow tube configured to supply a coolant fluid into the cooling chamber; and
   an outflow tube configured to dispense the coolant fluid from the cooling chamber.

9. The electrosurgical device of claim 8, further comprising:
   a coolant source to supply the coolant fluid.

10. The electrosurgical device of claim 1, wherein the shell assembly is coupled to a distal end of the electrically-conductive layer of the balun.

11. The electrosurgical device of claim 1, wherein the dielectric layer of the balun extends distally beyond a distal end of the electrically-conductive layer of the balun.

12. A method of manufacturing an electrosurgical device, comprising the steps of:
   providing a coaxial feedline having an inner conductor, an outer conductor, and a dielectric material disposed therebetween;
   joining an electrically-conductive member to a distal end of the inner conductor at a distal end of the coaxial feedline;
   joining a balun to a distal portion of the outer conductor, the balun including a dielectric layer coaxially disposed around the distal portion of the outer conductor and an electrically-conductive layer coaxially disposed around a proximal portion of the dielectric layer;
   joining an electrically-conductive cylinder to a distal portion of the electrically-conductive layer of the balun;
   forming a dielectric structure having a proximal end disposed substantially adjacent to a distal end of the electrically-conductive cylinder, wherein the dielectric structure longitudinally extends from the distal end of the electrically-conductive cylinder to a distal end of the electrically-conductive member;
   joining an elongated handle assembly to the outer conductor at a distal end of the coaxial feedline, wherein the handle assembly is disposed proximal to the dielectric structure; and
   joining a shell assembly to a distal end of the elongated handle assembly, wherein the shell assembly is coupled to a distal portion of the balun.

13. The method of manufacturing an electrosurgical device in accordance with claim 12, wherein the dielectric structure includes a cap of dielectric material configured to cover a distal end of the electrically-conductive member.

14. The method of manufacturing an electrosurgical device in accordance with claim 12, wherein the shell assembly includes an inner portion and an outer portion disposed about the inner portion.

15. The method of manufacturing an electrosurgical device in accordance with claim 14, wherein the outer portion of the shell assembly includes an electrically conductive material and the inner portion of the shell assembly includes a dielectric material.

16. The method of manufacturing an electrosurgical device in accordance with claim 14, wherein the inner portion of the shell assembly includes a flat planar surface having a recess defined therein.

17. The method of manufacturing an electrosurgical device in accordance with claim 16, wherein the recess is configured to receive at least a portion of the dielectric structure.

18. The method of manufacturing an electrosurgical device of claim 12, wherein the shell assembly is coupled to a distal end of the electrically-conductive layer of the balun.

19. The method of manufacturing an electrosurgical device of claim 12, wherein the dielectric layer of the balun extends distally beyond a distal end of the electrically-conductive layer of the balun.

* * * * *